US010412972B2

(12) United States Patent
Pathak et al.

(10) Patent No.: US 10,412,972 B2
(45) Date of Patent: Sep. 17, 2019

(54) GRANULE FORMULATIONS AS BIOCHEMICAL AGRICULTURAL PRODUCTS

(71) Applicant: Marrone Bio Innovations, Inc., Davis, CA (US)

(72) Inventors: Pankaj Pathak, Davis, CA (US); Rich La, Davis, CA (US); Michael Maurer, Davis, CA (US); Garrett Sell, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 0 days.

(21) Appl. No.: 15/515,198

(22) PCT Filed: Sep. 22, 2015

(86) PCT No.: PCT/US2015/051319
§ 371 (c)(1),
(2) Date: Mar. 29, 2017

(87) PCT Pub. No.: WO2016/057203
PCT Pub. Date: Apr. 14, 2016

(65) Prior Publication Data

US 2017/0215430 A1 Aug. 3, 2017

Related U.S. Application Data

(60) Provisional application No. 62/060,447, filed on Oct. 6, 2014, provisional application No. 62/133,035, filed on Mar. 13, 2015.

(51) Int. Cl.
*A01N 63/00* (2006.01)

(52) U.S. Cl.
CPC .................................... *A01N 63/00* (2013.01)

(58) Field of Classification Search
CPC ...................................................... A01N 63/00
See application file for complete search history.

(56) References Cited

U.S. PATENT DOCUMENTS 6,087,306 A * 7/2000 Bell ...................... A01N 25/14 504/367
2012/0100236 A1* 4/2012 Asolkar ................ A01N 43/90 424/780
2014/0227228 A1 8/2014 Asolkar et al.

FOREIGN PATENT DOCUMENTS

CN 101889586 B 1/2014
CN 103636599 A 3/2014
WO 2009093257 A2 7/2009
(Continued)

OTHER PUBLICATIONS

PCT/US2015/051319 Search Report and Written Opinion [KIPO] dated Dec. 7, 2015.

*Primary Examiner* — Johann R Richter
*Assistant Examiner* — Danielle Sullivan
(74) *Attorney, Agent, or Firm* — Chainey P. Singleton; Ying-Horng Liu

(57) ABSTRACT

The present disclosure includes the composition and methods of a granule formulation consist using a liquid biological active that has great handling properties yet still efficacious. The biological active is absorbed into or spray onto a mixture of carriers, dispersants, and/or wetting agents. When the product is formulated as a granule, it has good durability and does not dust which increases handleability of the product during application.

7 Claims, 22 Drawing Sheets

(56) References Cited

FOREIGN PATENT DOCUMENTS

| | | | |
|---|---|---|---|
| WO | WO2012/037352 | * | 3/2012 |
| WO | 2014147528 | A1 | 9/2014 |

* cited by examiner

GRANULAR FORMULATIONS AND CONCENTRATE (CORN)

GRANULE FORMULATIONS AS BIOCHEMICAL AGRICULTURAL PRODUCTS

TECHNICAL FIELD OF THE INVENTION

The present disclosure relates in general to the field of compositions and methods for formulating granules using a liquid biological suspension as the active as biopesticides to improve handling of the product.

BACKGROUND ART

Biopesticide formulations are generally designed based on customer needs and the physiochemical properties of the active ingredients, for example, the solubility of the active ingredient in water or non-aqueous solvents. There are two major categories of formulations, solid formulations and liquid formulations.

Solid formulations, such as water dispersible granule (WDG) and dispersible granules (DG), containing microbial active ingredients are seeing increased use today because of their relative safety compared to liquid formulations and the advantages they offer with regard to cost saving in packing and transportation, and the environmental benefits of eliminating the use of organic solvents. WDG formulations are designed to readily disperse on contact with the water carrier in a spray tank and provide equivalent performance to an emulsifiable concentrate product. DG formulations are normally designed for broadcast application without prior dilution in a carrier such as water. Granule products may be used for insect, weed, fungal pathogen and nematode control in both water and non-water applications. However, the microbial based granules are not typically readily to dissolve in water.

For example, *Chromobacterium subtsugae* strain PRAA4-1 (Grandevo®) is a gram-negative, violet-pigmented bacterium that was isolated from soil under an eastern hemlock (*Tsuga Canadensis*) in the Catoctin Mountain region of central Maryland. The United States Department of Agriculture found this isolate of *Chromobacterium subtsugae* to be orally toxic to Colorado potato beetle (*Leptinotarsa decemlineata*) larvae, live small hive beetle (*Aethina tumida*) larvae, southern corn rootworm (*Diabrotica undecimpunctate*) larvae and adults, and southern green stink bug (*Nezara viridula*) adults. Additional testing has shown that a *Chromobacterium subtsugae* strain PRAA4-1 treated diet resulted in reduced feeding in beet armyworm (*Spodoptera exigua*), cabbage looper (*Trichoplusia ni*), tobacco budworm (*Heliothis virescens*), diamondback moth (*Plutella xylostella*), and southern corn rootworm. Furthermore, this testing has suggested this microbe's insecticidal activity is due to reduction in weight or inhibition of feeding.

In another example, *Bacillus amyloliquefaciens* and *Bacillus megaterium* are gram-positive, spore-forming bacteria that were isolated from the soil. There is a large body of literature reporting the potential use of rhizosphere-associated bacteria in stimulating plant growth (Farah, Iqbel et al. 2008). These bacteria have plant growth promoting traits such as production of indoleactic acid, ammonia, hydrogen cyanide, siderophore, phosphate solubilization and antifungal activity.

Yet in another example, *Pseudomonas fluorescens* is a gram-negative bacterium that is found protecting the roots of plants from plant diseases. Previous work by the New York State Museum had isolated and identified a bacterial strain of *Pseudomonas fluorescens* (CL0145A) that can be applied as a dead cell mass—its highly selective biotoxin killed zebra mussels after three hours in one application but, unlike chlorine, did not kill any non-target species tested. Upon treatment, zebra mussels filter water treated with toxic CL0145A cell particles and pass those particles through their digestive system which gets destroyed.

Yet in another example, *Burkholderia rinojensis* isolate A396 is a gram-negative, straight rod bacterium that was isolated from the soil near the Rinoji Temple in Nikko, Japan by Marrone Bio Innovations. Contact and feeding bioassays reveal effective insecticidal and miticidal activities against beet armyworms (*Spodoptera exigua*) and two-spotted spider mites (*Tetranychus urticae*), respectively. Furthermore, these results suggest ingestion and contact as two mechanisms of action that cause larvae discoloration, stunted growth, molting issues, exoskeleton disintegration, and mortality.

Thus, there is a need to find formulations that can readily be dissolved in water.

DISCLOSURE OF THE INVENTION

In one aspect, the present disclosure provides the methods and composition of improving the handling properties with different types of biological granules using the micro-organisms in form of solid or liquid.

In another aspect, described herein are methods of improving the dispersion properties in water of a fermentation solid containing granule and compositions of such a granule. The described granule exhibits improved physical stability and improved dispersibility in water.

In one aspect, the present disclosure contains a composition that improves the dispersion properties in water comprising about 0.1-30 weight percent of fermentation solids from a microbe, about 10-20 weight percent of MCC, about 1-10 weight percent of CS, about 1-20 weight percent of AMS, about 1-10 weight percent of B3A, about 1-5 weight percent of SLS, and about 1-15 weight percent of K80B. The composition can further comprise about 0.05-1 weight percent of AOR-90.

In another aspect, the microbe can comprise *Chromobacterium subtsugae* strain PRAA4-1, *Bacillus amyloliquefaciens, Bacillus megaterium, Pseudomonas fluorescens*, or *Burkholderia rinojensis* isolate A396.

Yet in another aspect, the present disclosure describes a method of using a composition with improved dispersion properties in water of fermentation solids from a microbe having the steps of obtaining a mixture having the composition of about 0.1-30 weight percent of fermentation solids from a microbe, about 10-20 weight percent MCC, about 1-10 weight percent CS, about 1-20 weight percent AMS, about 1-10 weight percent B3A, about 1-5 weight percent SLS, and about 1-15 weight percent K80B; mixing the composition with water, and spraying said mixture to one or more plants or substrates. The composition can further comprise about 0.05-1 weight percent AOR-90.

In one aspect, the present disclosure describes a water dispersible granule having about 0.1-40 weight percent of fermentation solids from *Chromobacterium subtsugae*, about 10-20 weight percent clay, about 0.1 to 10 weight percent lignin sulfonate, about 0.1 to 10 weight percent Sodium Lauryl Sulfate, about 10 to 30% weight percent Ammonium Sulfate, about 10 to 20 weight percent Microcrystalline Cellulose, and about 5 to 15 weight percent of Croscarmellose Sodium; mixing the composition with water, and spraying said mixture to one or more plants or substrates.

In another aspect, the present disclosure describes a method of using a composition, said composition includes about 0.1-40 weight percent of fermentation solids from *Chromobacterium subtsugae*, about 10-20 weight percent clay, about 0.1 to 10 weight percent lignin sulfonate, about 0.1 to 10 weight percent Sodium Lauryl Sulfate, about 10 to 30% weight percent Ammonium Sulfate, about 10 to 20 weight percent Microcrystalline Cellulose, and about 5 to 15 weight percent of Croscarmellose Sodium.

DESCRIPTION OF THE DRAWINGS

For a more complete understanding of the features and advantages of the present invention, reference is now made to the detailed description of the invention along with the accompanying figures and in which.

DESCRIPTION OF THE INVENTION

Figure 1:
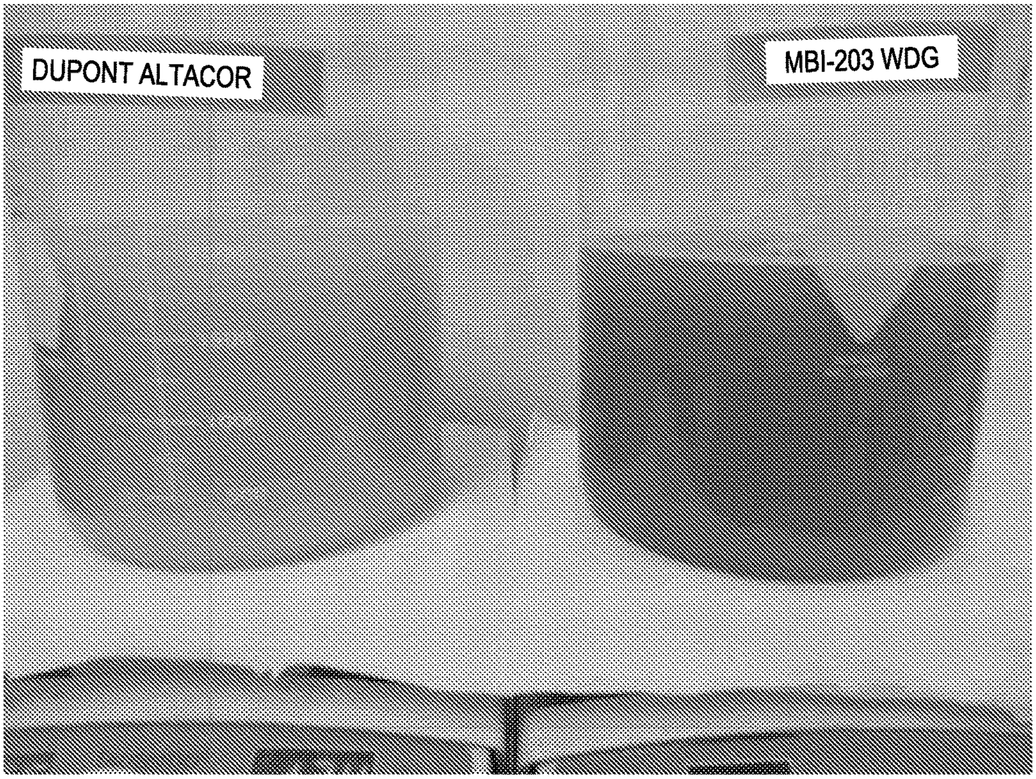
FIG. 1. Side view comparison of DuPont Altacor® and WDGE using *Chromobacterium subtsugae* after 3 minutes.
Figure 2:
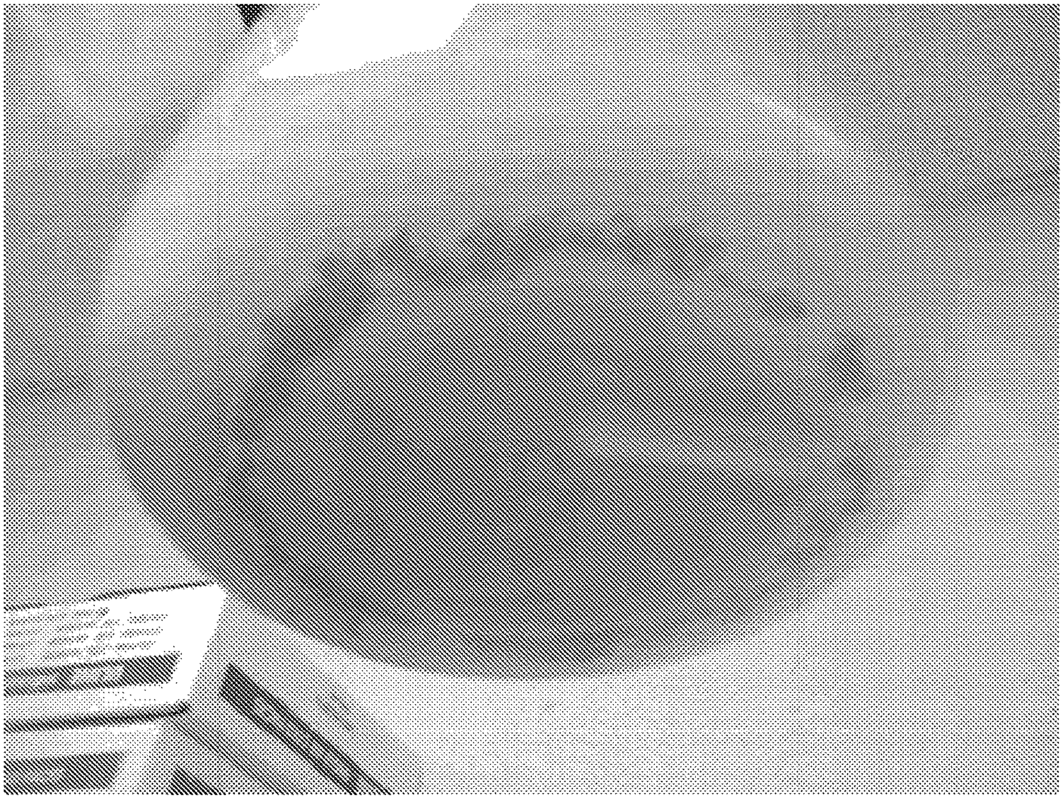
FIG. 2. Bottom view of DuPont Altacor® after 3 minutes shows a significant amount of residue.
Figure 3:
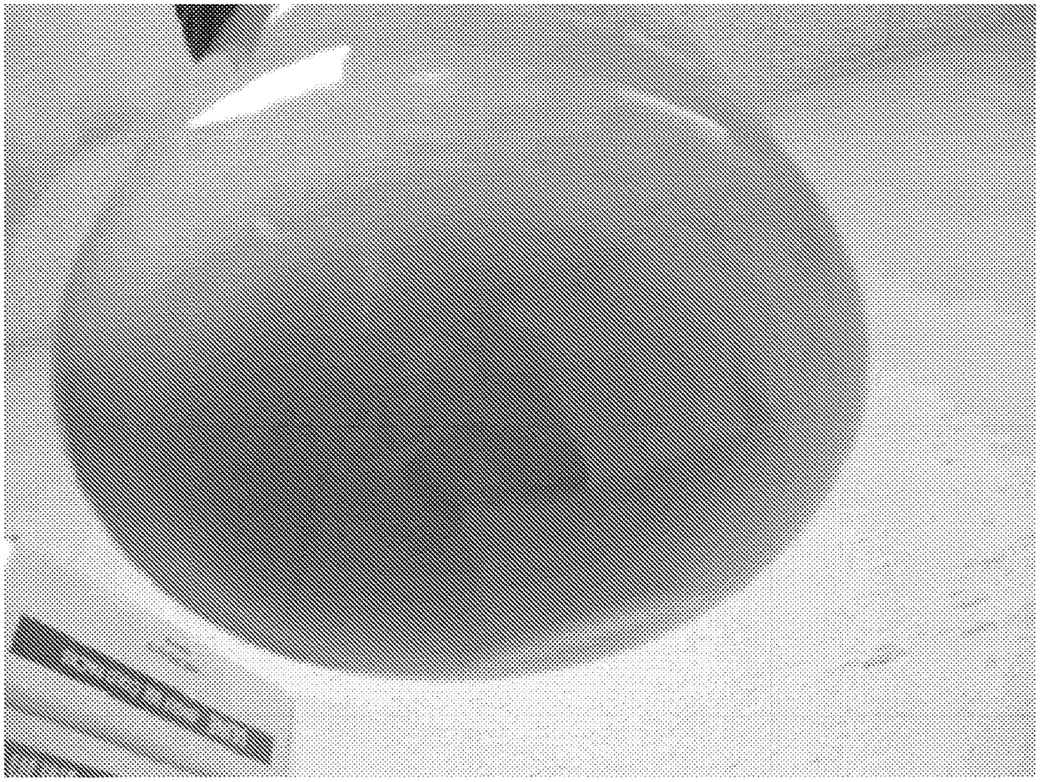
FIG. 3. Bottom view of WDGE prototype using *Chromobacterium subtsugae* after 3 minutes has no residues.
Figure 4:
FIG. 4. 300-micron sieve displays no residues from Altacor® solution.
Figure 5:
FIG. 5. 300-micron sieve displays no residues with the solution of WDGE using *Chromobacterium subtsugae.*
Figure 6:
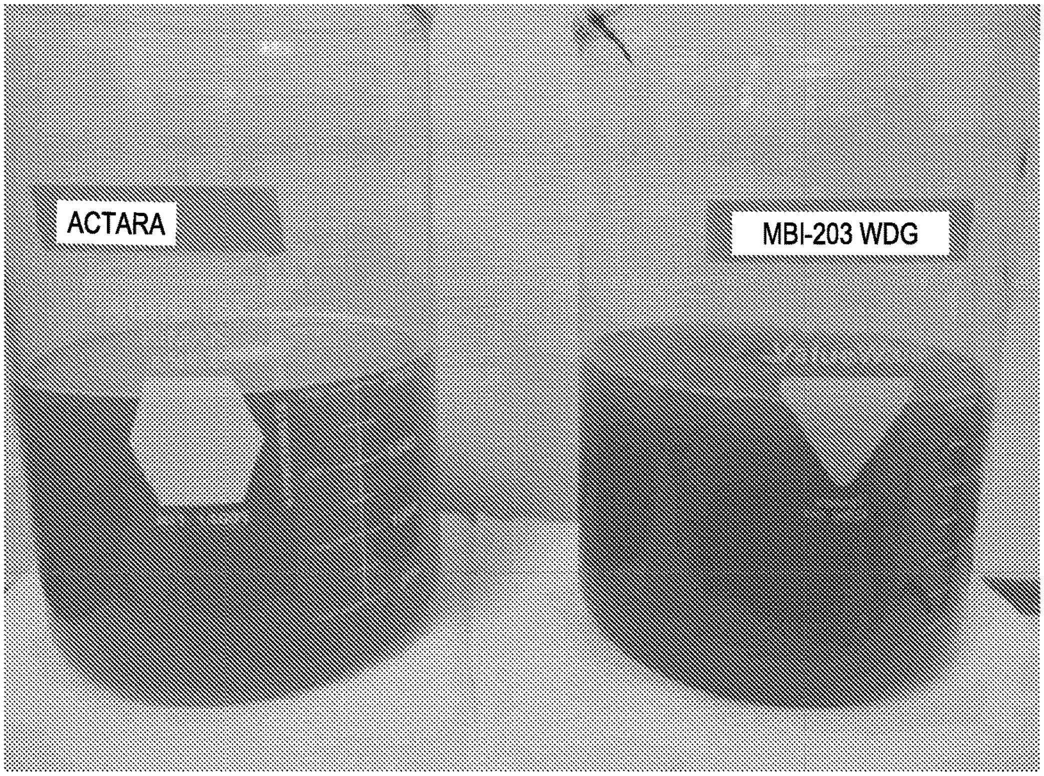
FIG. 6. Side view comparison of Sygenta Actara® and WDGE Prototype after 3 minutes.
Figure 7:
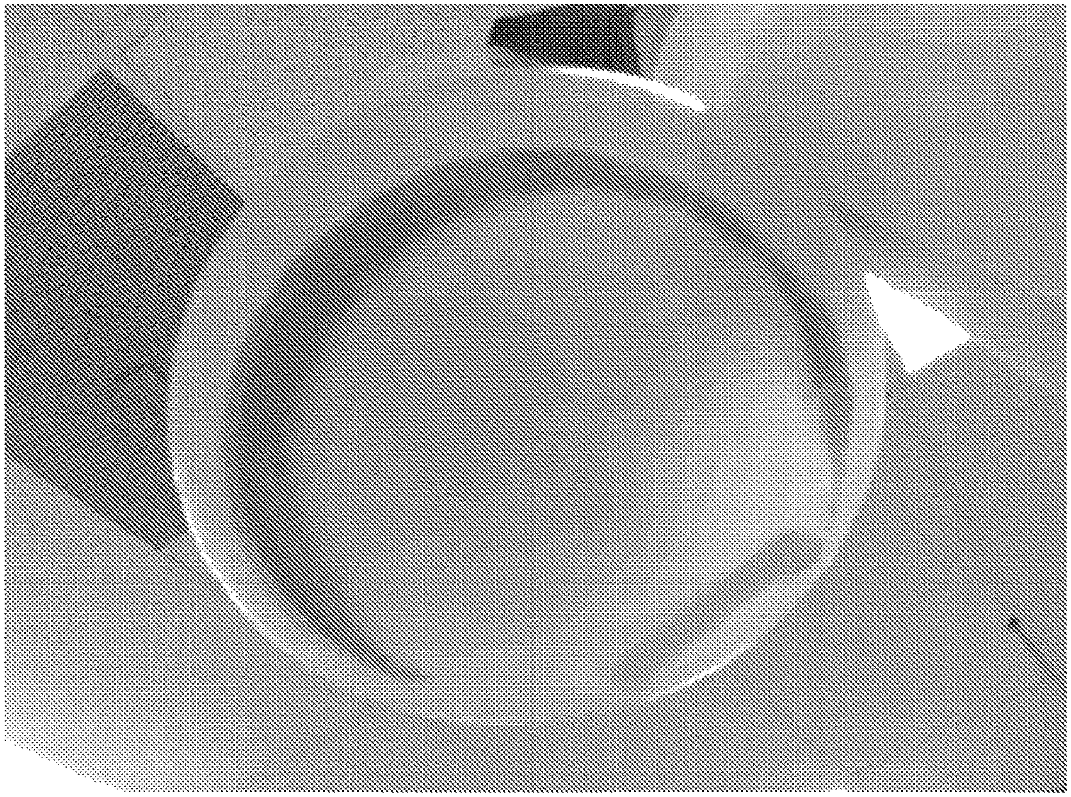
FIG. 7. Bottom view of Sygenta Actara® after 3 minutes shows a significant amount of residue.
Figure 8:
FIG. 8. Bottom view of WDGE prototype after 3 minutes has no residues.
Figure 9:
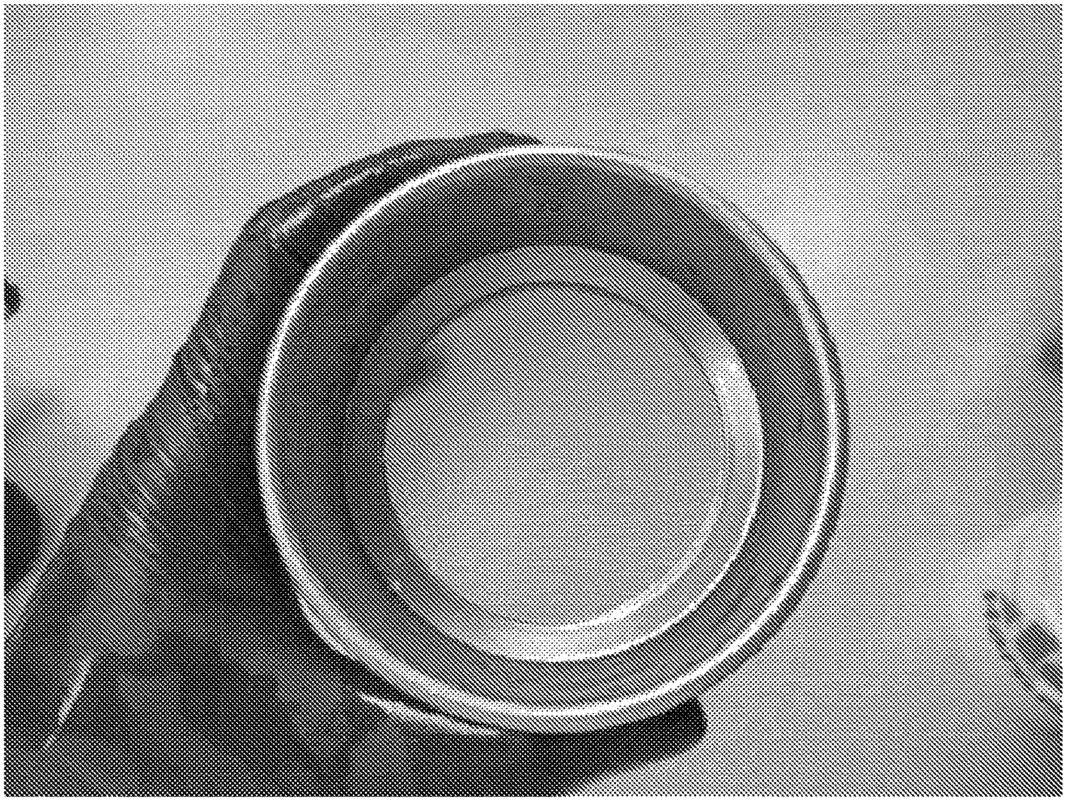
FIG. 9. 300-micron sieve displays no residues from Altacor® solution.
Figure 10:
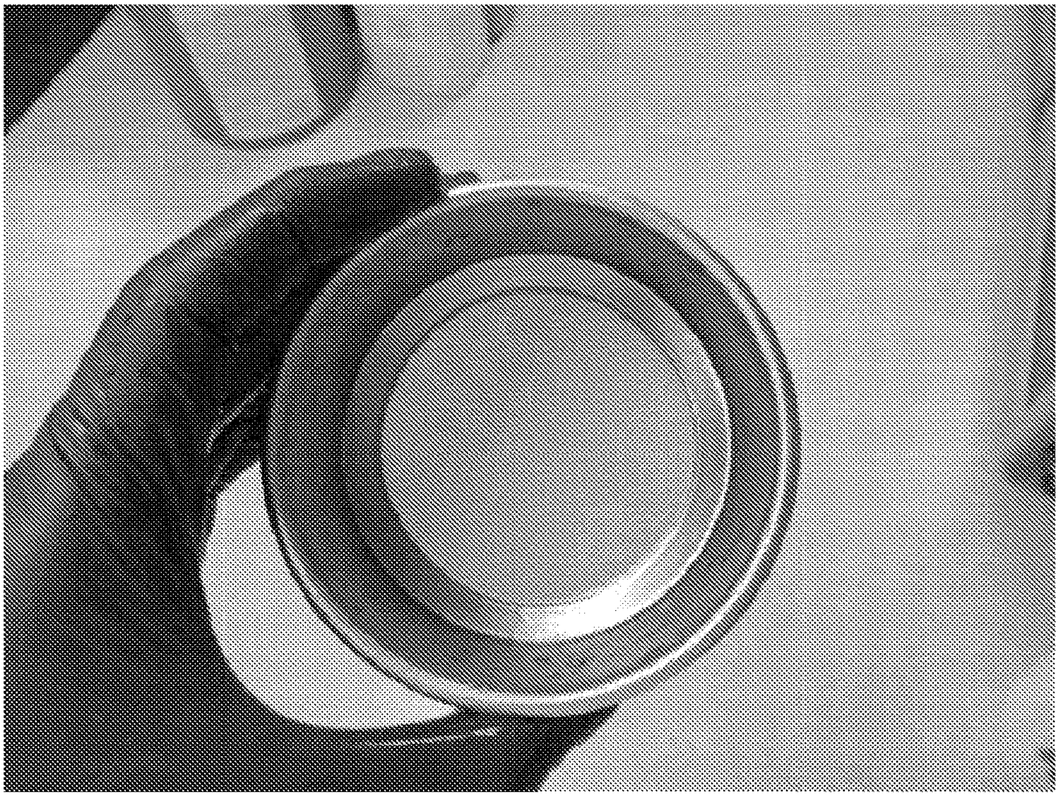
FIG. 10. 300-micron sieve displays no residues with the solution of WDGE using *Chromobacterium subtsugae.*

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "fermentation solids", "cell paste", or "TGAI" (Technical Grade Active Ingredient) can be used interchangeably, and include from very soluble compounds (e.g., free sugars, glycosides, acids, amine acids, and others) to very hydrophobic compounds (e.g., chlorophylls, long chain fatty acids, violacein and others).

Water dispersible granules formulations include but are not limited to wettable powders (WP).

As used herein, "about" is defined as plus or minus 50% of a given number.

Agricultural granules containing microbial based active ingredients can also contain inert ingredients such as solid carriers, surfactants, adjuvants, binders and the like. These inert ingredients can include, for example, clays, starches, silicas, sulphates, chlorides, lignosulfonates, carbohydrates, alkylated celluloses, xanthum gums and guaseed gums, and synthetic polymers such as polyvinyl alcohols, sodiumpolyacrylates, polyethylene oxides, polyvinylpyrrolidones and urea/formaldehyde polymers. The active ingredients contained in WG products can further include herbicides, insecticides, fungicides, plant growth regulators and safeners.

In one aspect, the present disclosure begins by solving the challenges in current commercial Grandevo® (*Chromobacterium subtsugae*) formulation, which is a biological wettable powder insecticide. In some instance, Grandevo® displays poor field application due to its dustiness and dispersion resistance, although the efficacy is not lost. Thus, the present disclosure presents reformulation that result in at least about ten-fold improvement in dispersibility from the current commercial Grandevo®. From the reformulation of Grandevo®, for example, it is shown herein that Ammonium Sulfate not only remediates hard water, but it improves dispersibility as well. After working with different excipients and inspired by the reformulated Grandevo® composition, the present disclosure presents a water dispersible granule formulation with a relatively high amount of active and fast dispersion properties.

The water dispersible granules were benchmarked in a timed dissolution test with the following commercial granules: Altacor® by Dupont, Actara® by Sygenta, and DiPel® by Valent. Not only these granules had fast dissolution, they remain efficacious. In addition to water dispersible granules, dispersible granules for turf application were developed to improve handling and efficacy of the product.

Formulations

Water Dispersible Granules (WDG)

These are the formulations that use carriers (e.g. kaolin, cellulose, light calcium, white carbon black, silica soil algae . . . etc.) to absorb or stick the active ingredients, and use dispersants and other adjuvants to help disperse in water, resulting in spraying solution.

Example 1: Water Dispersible Granule Using *Chromobacterium subtsugae*

Preparation of a water dispersible granule using a biological, *Chromobacterium subtsugae*, with insecticidal properties (hereinafter referred to as "CB4 WDGE"):

Wet Granulation (1-7 & 10-38)

Step A) Fermentation solids of *Chromobacterium subtsugae* with a dry total weight ranging from 10% to 15% is centrifuged to a 20× concentration; step B) Specified percentages of the following compositions (Tables 1-3) were mixed into an uniform powder; step C) "A" is combined with the mixture of "B" to make a dough mixture; step D) If necessary, moisture content from C is further removed to 25% to 35%; step E) "D" is extruded in a screw dome or basket extruder; step F) "E" is dried to a moisture content less than 10%.

Dry Mix Granulation (8-9 & 39-46)

Step A) Fermentation solids of *Chromobacterium subtsugae* with a dry total weight ranging from 10% to 15% are spray dried; step B) Specified percentages of the following compositions were mixed into a uniform powder; step C) "A", "B", and water are combined to form a dough mixture; step D) "C" is extruded in a screw dome or basket extruder; step E) "D" is dried to a moisture content less than 10%.

TABLE 1

Composition of CB4 WDGE using wet granulation

| | Final Dried Contents | | | | | | | Dissolution |
|---|---|---|---|---|---|---|---|---|
| | TGAI | | Stabilizer | Carrier | | | | |
| | Cell | | | | Dispersant | | | 1-Best |
| # | Paste | DF7 | PEG | MCC | CS | Hubersorb | AMS | 5-Worst |
| 1 | 30% | 0% | 0% | 36.5% | 5% | 18.3% | 0% | 5 |
| 2 | 30% | 0% | 0% | 39.6% | 5% | 21.4% | 12% | 5 |
| 3 | 30% | 0% | 0% | 17.5% | 5.5% | 12% | 35% | 3 |
| 4 | 30% | 0% | 20% | 17.5% | 5.5% | 12% | 0% | 3 |
| 5 | 30% | 0% | 0% | 40% | 5% | 0% | 20% | 2 |
| 6 | 30% | 0% | 5% | 40% | 5% | 0% | 20% | 2 |
| 7 | 30% | 0% | 0% | 40% | 5% | 0% | 25% | 1 |

TABLE 2

Composition of CB4 WDGE using wet granulation

| | Final Dried Contents | | | | | | | | | | | | | |
|---|---|---|---|---|---|---|---|---|---|---|---|---|---|---|
| | TGAI Cell | Carrier | Dispersant | | | | Wetting Agent | | Filler | | | | Anti-foam | Dissolution 1-Best |
| # | Paste | MCC | CS | CMC | AMS | B3A | NSC | SLS | Starch | K80B | RF | B | AOR-90 | 5-Worst |
| 10 | 30% | 15% | 5% | 0% | 20% | 0% | 8% | 2% | 5% | 0% | 0% | 0% | 0% | 5 |
| 11 | 30% | 15% | 5% | 0% | 20% | 0% | 8% | 2% | 0% | 0% | 0% | 0% | 0% | 5 |
| 12 | 30% | 15% | 10% | 0% | 0% | 0% | 8% | 2% | 15% | 0% | 0% | 0% | 0% | 5 |
| 13 | 30% | 15% | 5% | 0% | 20% | 0% | 8% | 2% | 20% | 0% | 0% | 0% | 0% | 5 |
| 14 | 30% | 15% | 5% | 0% | 20% | 0% | 0% | 0% | 0% | 0% | 0% | 0% | 0% | 5 |
| 15 | 28.6% | 15% | 4.8% | 0% | 19% | 0% | 7.6% | 1.9% | 0% | 9.4% | 0% | 0% | 0% | 3 |
| 16 | 30% | 15% | 5% | 0% | 20% | 0% | 8% | 2% | 0% | 0% | 10% | 0% | 0% | 3 |
| 17 | 30% | 15% | 5% | 0% | 20% | 0% | 8% | 2% | 0% | 0% | 20% | 0% | 0% | 5 |
| 18 | 30% | 12% | 5% | 0% | 20% | 0% | 8% | 2% | 0% | 0% | 10% | 0% | 0% | 5 |
| 19 | 30% | 15% | 10% | 0% | 20% | 0% | 8% | 2% | 0% | 0% | 15% | 0% | 0% | 2 |
| 20 | 30% | 15% | 10% | 0% | 20% | 0% | 8% | 2% | 0% | 15% | 0% | 0% | 0% | 2 |
| 21 | 30% | 15% | 10% | 0% | 20% | 0% | 8% | 2% | 0% | 0% | 0% | 0% | 0% | 2 |
| 22 | 30% | 15% | 5% | 5% | 20% | 0% | 8% | 2% | 0% | 15% | 0% | 0% | 0% | 3 |
| 23 | 30% | 20% | 10% | 0% | 20% | 10% | 8% | 2% | 0% | 0% | 0% | 0% | 0% | 2 |
| 24 | 30% | 15% | 10% | 0% | 20% | 10% | 8% | 2% | 0% | 5% | 0% | 0% | 0% | 3 |
| 25 | 30% | 15% | 10% | 0% | 15% | 10% | 8% | 2% | 0% | 10% | 0% | 0% | 0% | 4 |
| 26 | 30% | 15% | 10% | 0% | 20% | 5% | 0% | 5% | 0% | 15% | 0% | 0% | 0% | 1 |
| 27 | 30% | 15% | 10% | 0% | 20% | 10% | 0% | 5% | 0% | 10% | 0% | 0% | 0% | 2 |
| 29 | 30% | 15% | 10% | 0% | 20% | 5% | 0% | 5% | 0% | 15% | 0% | 0% | 0.1% | 1 |
| 30 | 30% | 15% | 10% | 0% | 20% | 5% | 0% | 5% | 0% | 0% | 0% | 15% | 0% | 2 |

TABLE 3

Composition of CB4 WDGE using dry mix granulation

| | Final Dried Contents | | | | | | | | | | | | Dissolution |
|---|---|---|---|---|---|---|---|---|---|---|---|---|---|
| | TGAI | | | | | | | | Wetting | | | | |
| | SDP | | Stabilizer | Carrier | Dispersant | | | | Agent | | Filler | Glidant | 1-Best |
| # | Cells | DF7 | PEG | MCC | CS | CMC | AMS | B3A | NSC | SLS | K80B | FS | 5- Worst |
| 1 | 0% | 100% | 0% | 0% | 0% | 0% | 0% | 0% | 0% | 0% | 0% | 0% | 5 |
| 2 | 0% | 95% | 0% | 0% | 5% | 0% | 0% | 0% | 0% | 0% | 0% | 0% | 5 |
| 3 | 30% | 0% | 0% | 13% | 5% | 0% | 20% | 10% | 8% | 2% | 10% | 2% | 4 |
| 4 | 30% | 0% | 0% | 0% | 1% | 0% | 20% | 10% | 8% | 2% | 27% | 2% | 4 |
| 5 | 30% | 0% | 0% | 13% | 5% | 0% | 20% | 10% | 8% | 2% | 10% | 2% | 3 |

TABLE 3-continued

| Composition of CB4 WDGE using dry mix granulation | | | | | | | | | | | | | |
|---|---|---|---|---|---|---|---|---|---|---|---|---|---|
| | Final Dried Contents | | | | | | | | | | | | |
| | TGAI | | | | | | | | Wetting | | | | Dissolution |
| | SDP | | Stabilizer | Carrier | Dispersant | | | | Agent | | Filler | Glidant | 1-Best |
| # | Cells | DF7 | PEG | MCC | CS | CMC | AMS | B3A | NSC | SLS | K80B | FS | 5- Worst |
| 6 | 99% | 0% | 0% | 0% | 1% | 0% | 0% | 0% | 0% | 0% | 0% | 0% | 3 |
| 7 | 30% | 0% | 3% | 10% | 5% | 0% | 35% | 0% | 0% | 5% | 10% | 2% | 1 |
| 8 | 30% | 0% | 0% | 15% | 10% | 0% | 20% | 0% | 8% | 2% | 13% | 2% | 2 |
| 9 | 30% | 0% | 0% | 15% | 5% | 5% | 20% | 0% | 8% | 2% | 13% | 2% | 2 |

Cell paste, SDP cells, and DF7 are sources of actives in liquid, spray dried powder, and dry flowable; PEG is polyethylene glycol; MCC is microcrystalline cellulose; CS is croscarmellose sodium; CMC is carboxylmethyl cellulose; Hubersorb is calcium silicate; AMS is ammonium sulfate; NSC is sodium naphthalene sulfonate condensate; SLS is sodium lauryl sulfate; B3A is sodium lignin sulfonate; Starch is corn starch; RF is Rice Flour; B is Bentonite; K80B is kaolin clay; AOR-90 is Antifoam OR-90; FS is fumed silica.

Evaluation of Dispersion Properties of CB4 WDGE:

Dispersion of the CB4 WDGE was evaluated at 10-fold dilution with tap water (note: 10-fold dilution is the recommended application rate) in a 4-L beaker with a low stirring rate to simulate the agitation of a 100-gallon recirculation tank. Each water dispersible granule was given a maximum time of 3 minutes to disperse into the solution and then was passed through a 300 micron sieve (note: commonly used filter in water pumps and tanks). In addition, the formulation was compared to two commercial granules, Altacor® and Actara®. After 3 minutes, pictures of the side and the bottom of the beaker along with any residue were taken and are shown as FIGS. 1 to 5 (Altacor® vs. Prototype), FIGS. 6 to 10 (Actara® vs. Prototype), Cabbage Looper Bioassay The cabbage looper larvae were first instar old when treated. DiPel® from Valent at 100-fold dilution was used as a positive control. Treatments were prepared by applying 100 μL of the solution into a well with one late first instar cabbage looper larvae. They were incubated at 26° C., and LC50 and CLKU (Cabbage Looper Killing Units) were determined four days after treatment. The potency of the candidate is determined by comparing LC50s from the candidate and standard using the following equation: Potency (CLKU/mg)=LC50 Standard*potency of standard (CLKU/mg)/LC50 candidate. The potency of the standard is 11,000 CLKU/mg. Unformulated broths with equal to or greater than 500 CLKU/mg are considered acceptable and test samples with equal to or greater than 1000 CLKU/mg are considered acceptable. Formulated samples with an uncorrected mortality of greater than 80% at 8% concentration are considered acceptable. Samples with mortality below the established rates are considered inadequate and should be removed from further downstream processing.

TABLE 4

Comparison of efficacy of CB4-WDGE-1 toward Cabbage Looper Mortality Assay One - Diet Overlay

| Prototype # | $LC50_{sample}$ | $LC50_{standard}$ | Uncorrected Mortality @2% (sample) | Uncorrected Mortality @2% (standard) | Uncorrected Mortality @8% (sample) | Uncorrected Mortality @8% (standard) |
|---|---|---|---|---|---|---|
| 11 | 0.54 | 3.62 | 82.35 | 32.5 | 100 | 100 |
| 15 | 1.83 | | 47.37 | | 100 | |
| 16 | 1.73 | | 64.71 | | 100 | |
| 39 | 3.27 | 3.59 | 28.95 | 31.58 | 100 | 715 |
| 40 | 2.79 | | 47.5 | | 100 | |
| 43 | 2.74 | | 32.5 | | 100 | |
| 20 | 27 | | 44.12 | | 100 | |
| 27 | 1.42 | 6.33 | 69.44 | 7.5 | 100 | 65.79 |
| 29 | 1.59 | | 82.5 | | 97.5 | |
| 33 | 1.76 | | 47.37 | | 100 | |
| 34 | 1.61 | | 62.5 | | 100 | |
| 35 | 3.41 | 6.27 | 215 | 19.44 | 92.11 | 47.37 |
| 36 | 2.69 | 6.72 | 476 | 13.16 | 100 | 65.79 |
| 37 | 1.61 | | 58.33 | | 100 | |

Example 2: Water Dispersible Granule Using *Bacillus amyloliquefaciens*

Preparation of a water dispersible granule using a biological, *Bacillus amyloliquefaciens*, with growth promoting properties (hereinafter referred to as "BAM2 WDGE"):

Wet Granulation

A) Fermentation solids of *Bacillus amyloliquefaciens* with dry total weights ranging from 5% to 10% are centrifuged to 10×, 20×, and 45× concentrations; B) Specified percentages of the following compositions were mixed into a uniform powder; C) A is combined with B to make a dough mixture; D) If necessary, moisture from C is further removed to 25% to 35%; E) D is extruded in a screw dome or basket extruder; F) E is dried to a moisture content less than 10%.

TABLE 5

Composition of BAM2 WDGE.

| # | Final Dried Contents: Active: Whole Cell Broth | 45X Cell Concentrate | Carrier: HMAS | BCA | MCC | Dispersant: CS | AMS | Wetting Agent: SLS | Filler: K80B | Dissolution 1-Best 5-Worst |
|---|---|---|---|---|---|---|---|---|---|---|
| 1 | 0% | 16.7% | 66.7% | 16.7% | 0% | 0% | 0% | 0% | 0% | 3 |
| 2 | 7.3% | 0% | 0% | 0% | 26.5% | 13.3% | 26.5% | 6.6% | 19.9% | 2 |
| 3 | 14.6% | 0% | 0% | 0% | 22.7% | 11.4% | 22.7% | 5.6% | 17% | 1 |

Note:
Whole cell broth and cell concentrate are sources of active ingredients; HMAS is hydrous magnesium aluminum silicate; BCA is a calcium lignin sulfonate; MCC is microcrystalline cellulose; CS is a pharmaceutical grade of croscarmellose sodium; AMS is ammonium sulfate; SLS is sodium lauryl sulfate; K80B is a brand of kaolin clay.

Figure 11:
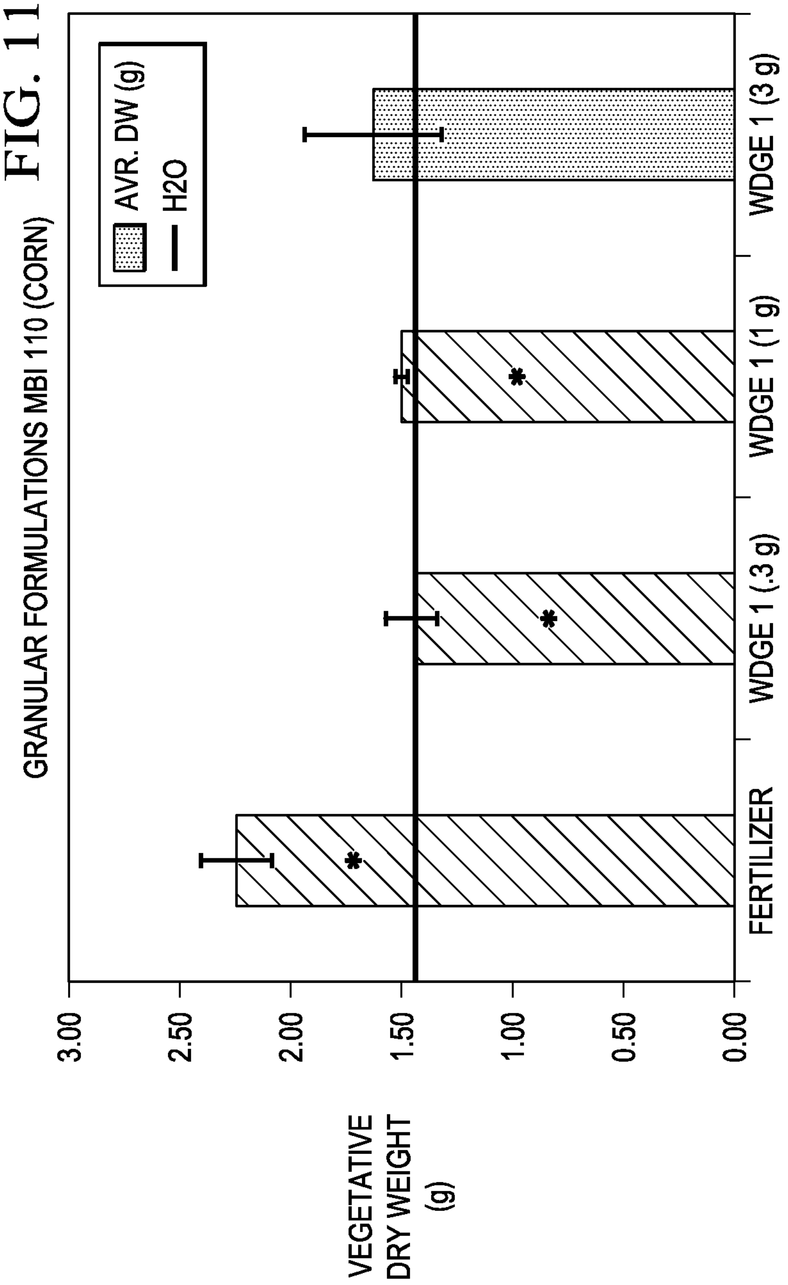
FIG. 11. Efficacy of WDGE using *Bacillus amyloliquefaciens*

Corn Drench Application: Experiments were conducted to confirm the growth promoters using drench as an application method. Plants 1-2 weeks old were drenched with 30 mL of inoculant suspension. The rates used were 0.3, 1, and 3 g EP/100 mL water using eight repetitions for each treatment. Each repetition consisted of three corn plants in a 3.5 inches pot. The negative control was drenched with 30 mL double distilled water and the positive controls were drenched with 30 mL of Miracle grow (25%) or 10× cell concentrate (fermentation control). The measured response was fresh and dry vegetative weights two weeks after inoculation. Results are depicted in FIG. 11.

Example 3: Water Dispersible Granule Using *Bacillus megaterium*

Preparation of a water dispersible granule using a biological, *Bacillus megaterium*, with growth promoting properties (hereinafter referred to as "MM2 WDGE"):

Wet Granulation

Step A) Fermentation solids of *Bacillus megaterium* with a dry total weight ranging from 5% to 10% are centrifuged to 10×, 20×, and 45× concentrations; step B) Specified percentages of the following compositions were mixed into a uniform powder; step C) "A" is combined with "B" to make a dough mixture; step D) If necessary, moisture from "C" is further removed to 25% to 35%; step E) "D: is extruded in a screw dome or basket extruder; step F) "E" is dried to a moisture content less than 10%.

Whole cell broth and cell concentrate are sources of the active ingredients; HMAS is a brand of hydrous magnesium aluminum silicate; BCA is a brand of calcium lignin sulfonate; PVP is polyvinylpyrrolidone; SA is Sodium Alginate.

Figure 12:
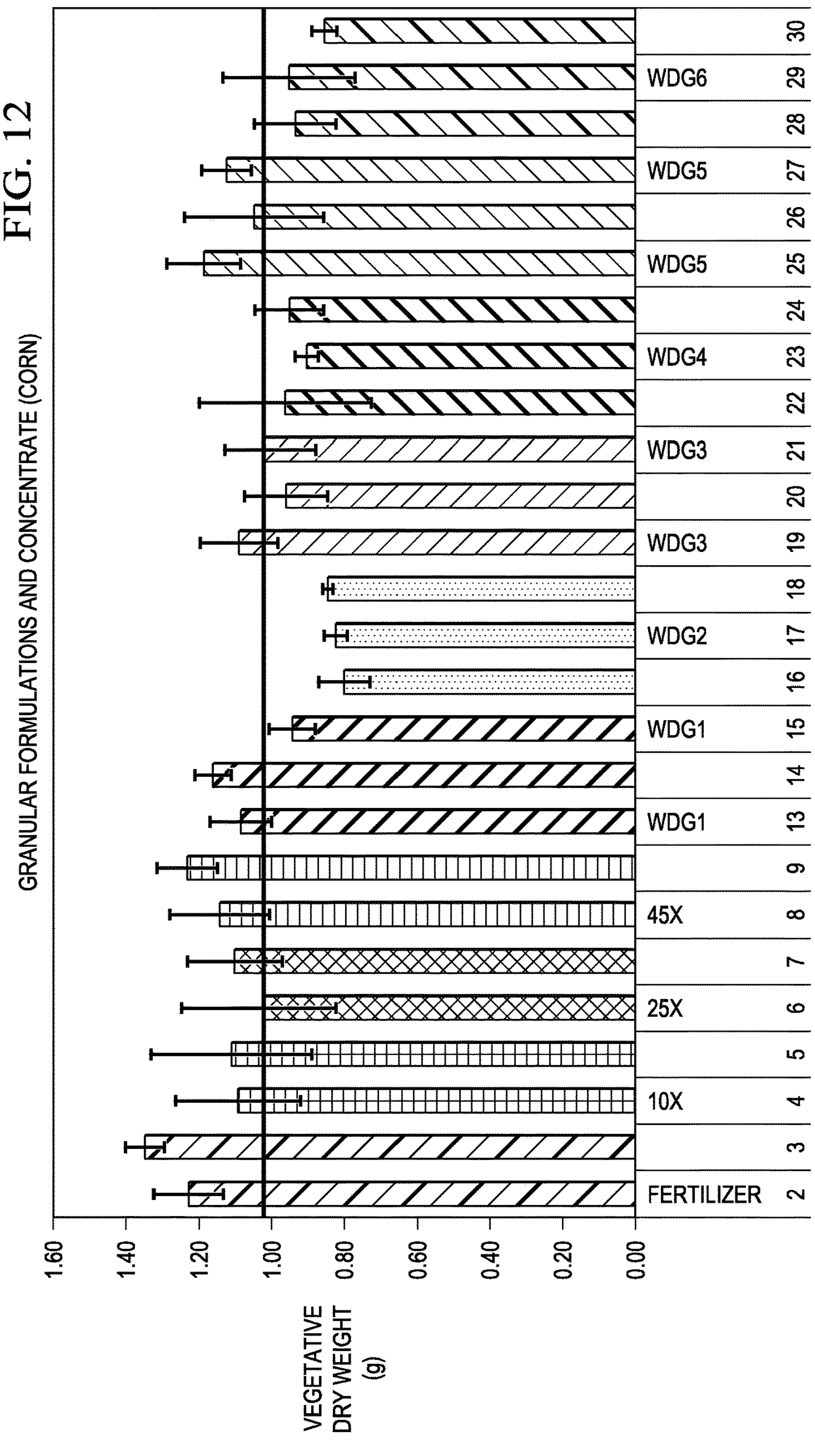
FIG. 12. Efficacy of WDGE using *Bacillus megaterium*
Figure 13:
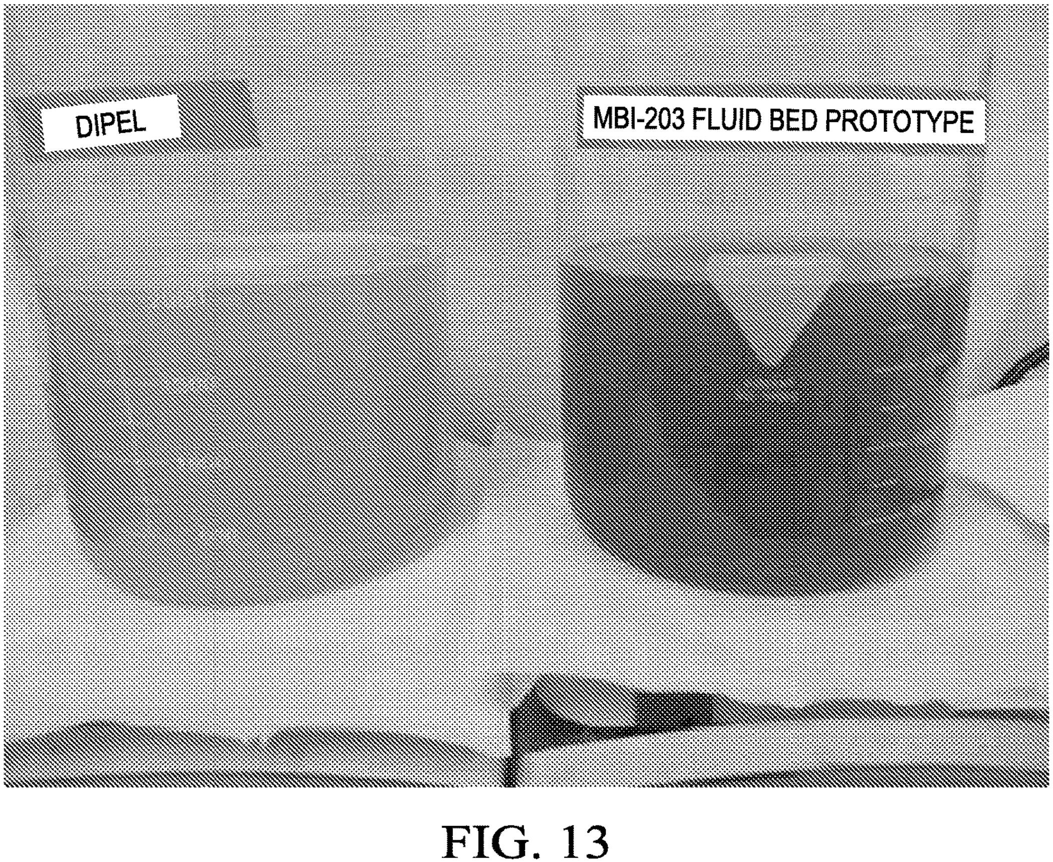
FIG. 13. Side view comparison of Valent DiPel® and WDGF Prototype after 3 minutes.

Corn Drench Application: Resulting data were shown to confirm the growth promoters using drench as an application method. Plants 1-2 weeks old were drenched with 30 mL of inoculant suspension. The rates used were 0.3, 1, and 3 g EP/100 mL water using eight repetitions for each treatment. Each repetition consisted of three corn plants in a 3.5 inches pot. The negative control was drenched with 30 mL double distilled water and the positive controls were drenched with 30 mL of Miracle grow (25%) or 10× cell concentrate (fermentation control). The measured response was fresh and dry vegetative weights 2 weeks after inoculation. Results are depicted in FIG. 12.

Example 4: Water Dispersible Granules Using *Chromobacterium subtsugae*

Preparation of a water dispersible granule using a biological, *Chromobacterium subtsugae* (hereinafter referred to as "CB4 WDGF-1": A) Fermentation solids of *Chromobacterium subtsugae* strain PRAA4-1 are mixed with the following compositions to form a uniform spray solution; B) A is sprayed onto the carrier which agglomerates to form water dispersible granules.

TABLE 6

Composition of MM2 WDGE.

| # | Final Dried Contents: Active: Whole Cell Broth | 10X Cell Concentrate | 20X Cell Concentrate | 45X Cell Concentrate | Carrier: HMAS | BCA | Lactose | Dispersant: PVP | SA | Dissolution 1-Best 5-Worst |
|---|---|---|---|---|---|---|---|---|---|---|
| 1 | 0% | 2.4% | 0% | 0% | 78.1% | 19.5% | 0% | 0% | 0% | 6 |
| 2 | 0% | 1.2% | 0% | 0% | 0% | 0% | 81.9% | 5.6% | 11.3% | 3 |
| 3 | 0% | 0% | 4.9%% | 0% | 76.1% | 19% | 0% | 0% | 0% | 5 |
| 4 | 0% | 0% | 2.4%% | 0% | 0% | 0% | 80.9% | 5.6% | 11.1% | 2 |
| 5 | 0% | 0% | 0% | 8.8% | 73% | 18.2% | 0% | 0% | 0% | 4 |
| 6 | 0% | 0% | 0% | 4.4% | 0% | 0% | 79.2% | 5.4% | 10.9% | 1 |

TABLE 7

Composition of CB4 WDGF-1.

| # | Final Dried Composition: Active Whole Cell Broth | Carrier: K80B | Carrier: D3560 | Carrier: Z5162 | Dispersant: B3A | Dispersant: PVP | Dispersant: P20 | Dispersant: P80 | Dispersant: Urea | Dispersant: T1004 | Dispersant: AM | Dispersant: AMS | Filler L | Wetting Agent SLS | Dissolution 1-Best 5-Worst |
|---|---|---|---|---|---|---|---|---|---|---|---|---|---|---|---|
| 1 | 26.8% | 70.9% | 0% | 0% | 1.9% | 0.1% | 0.4% | 0% | 0% | 0% | 0% | 0% | 0% | 0% | 8 |
| 2 | 51.5% | 0% | 0% | 36.4% | 5.3% | 1% | 0% | 0% | 5.3% | 0% | 0% | 0% | 0% | 0% | 7 |
| 3 | 48.8% | 0% | 0% | 40.7% | 5% | 0% | 0% | 0.5% | 0% | 0% | 0% | 0% | 5% | 0% | 6 |
| 4 | 22% | 73% | 0% | 0% | 1.1% | 0% | 0% | 0% | 0% | 1.1% | 3.3% | 0% | 0% | 0% | 5 |
| 5 | 26% | 58% | 0% | 0% | 2.6% | 0% | 0% | 0% | 0% | 0% | 0% | 5.1% | 0% | 8.6% | 4 |
| 6 | 43% | 0% | 0% | 29% | 4.3% | 0% | 0% | 0% | 0% | 0% | 0% | 8.7% | 0% | 14% | 3 |
| 7 | 47.2% | 0% | 0% | 35.6% | 4.9% | 0% | 0% | 0% | 0% | 0% | 0% | 9.8% | 0% | 2.5% | 2 |
| 8 | 49.3% | 0% | 0% | 29.6% | 5% | 0% | 0% | 0% | 0% | 0% | 0% | 9.9% | 0% | 6.3% | 1 |

Whole cell broth is a source of the active ingredients; K80B is kaolin clay; D3560 is dolomitic limestone; Z5162 is silica; B3A is sodium lignin sulfonate; PVP is polyvinylpyrrolidone; P20 is Polysorbate 20; P80 is Polysorbate 80; T1004 is Terwet 1004; AM is Atlox Metasperse; AMS is Ammonium Sulfate; L is Lactose; SLS is Sodium Lauryl Sulfate.

Figure 14:
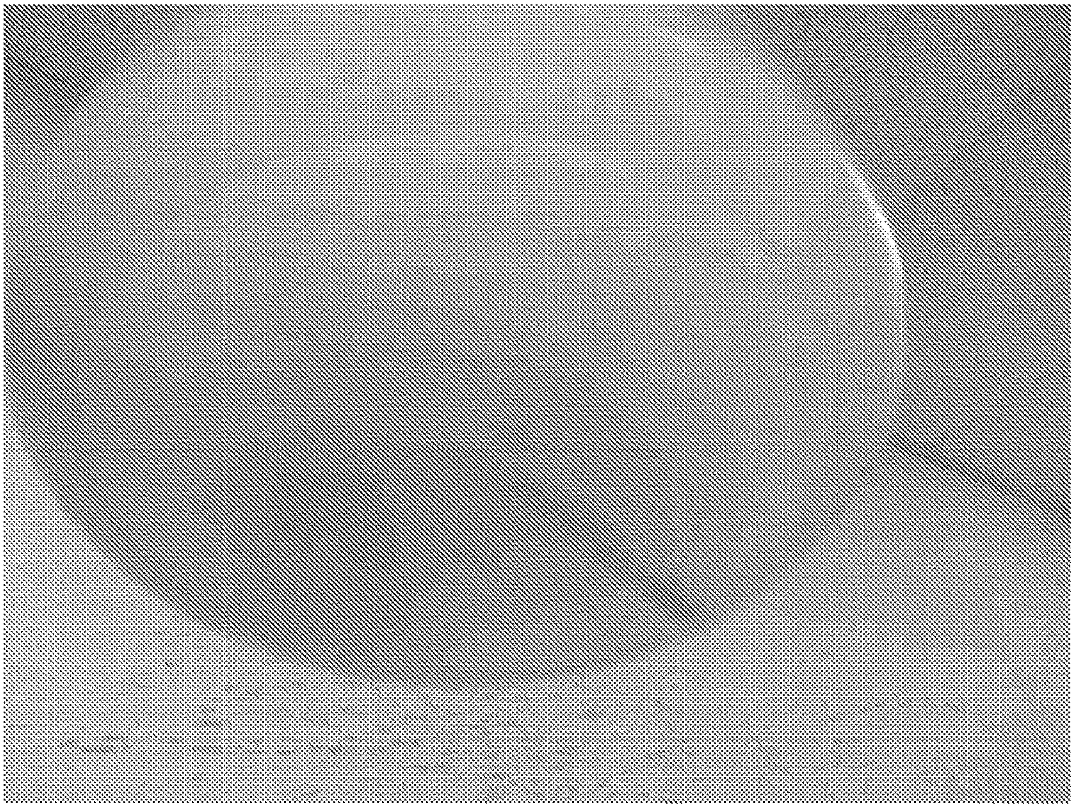
FIG. 14. Bottom view of DiPel® after 3 minutes has no residues.
Figure 15:
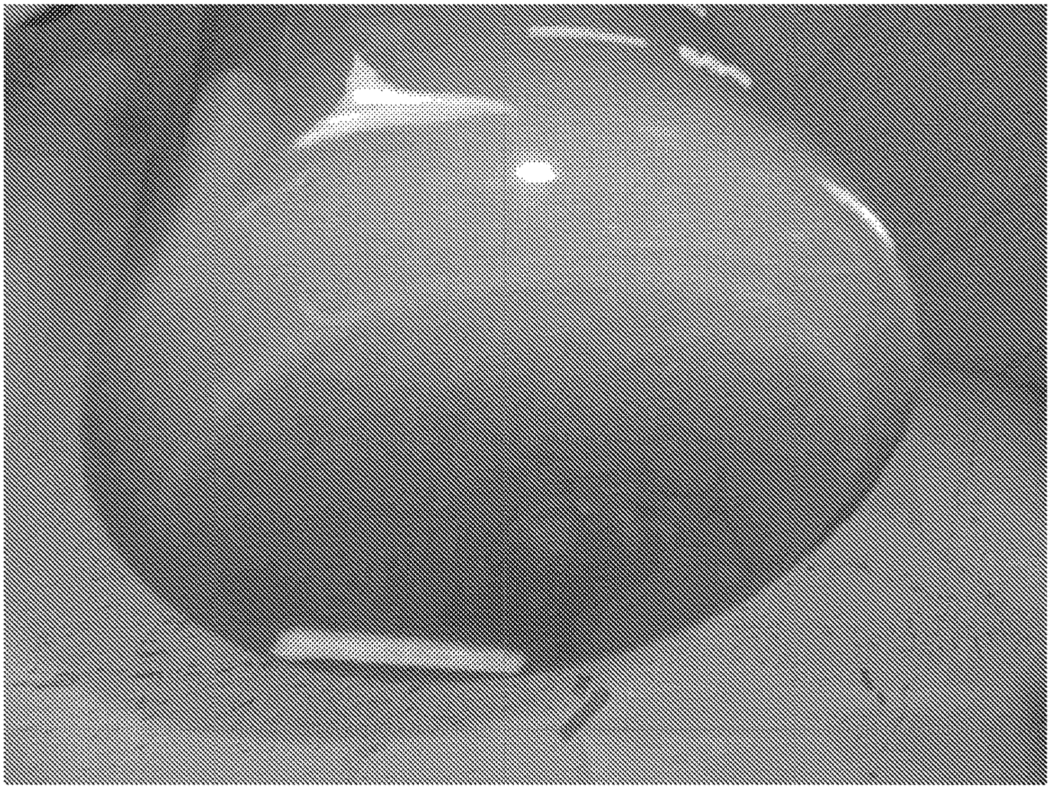
FIG. 15. Bottom view of WDGF using *Chromobacterium subtsugae* after 3 minutes has some residues.
Figure 16:
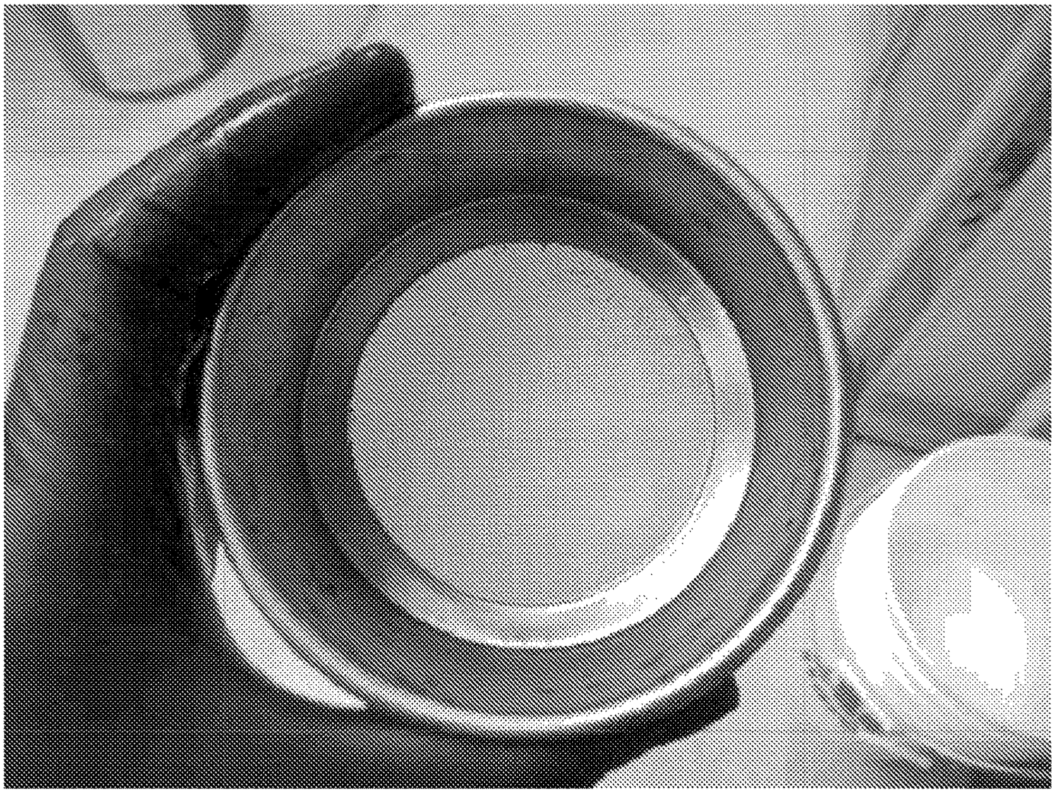
FIG. 16. 300-micron sieve displays minimal amounts of residue from the DiPel® solution.
Figure 17:
FIG. 17. 300-micron sieve displays minimal amounts of residue with the solution of the WDGF prototype using *Chromobacterium subtsugae.*

Evaluation of Dispersion Properties of CB4 WDGF-1:

Dispersion of the CB4 WDGE was evaluated at 10-fold dilution with tap water (note: 10-fold dilution is recommended application rate) in a 4-L beaker with a low stirring rate to simulate the agitation in a 100-gallon recirculation tank. Each water dispersible granule was given a maximum time of 3 minutes to disperse into the solution and was passed through a 300 micron sieve (note: commonly used filter in water pumps and tanks). In addition, the formulation was compared to a commercial granule, DiPel®. After 3 minutes, pictures of the side and the bottom of the beaker along with any residue on the sieve were taken and are shown in FIG. 14.

Cabbage Looper bioassay: The cabbage looper larvae were first instar old when treated. DiPel® from Valent at 100-fold dilution was used as a positive control. Treatments were prepared by applying 100 μL of the solution into a well with one late first instar cabbage looper larvae. Treatments were incubated at 26° C. and LC50 and CLKU (Cabbage Looper Killing Units) were determined 4 days after treatment. The potency of the candidate is determined by comparing LC50s from the candidate and standard using the following equation: Potency (CLKU/mg)=LC50 Standard*potency of standard (CLKU/mg)/LC50 candidate. The potency of the standard is 11,000 CLKU/mg. Unformulated broths with equal to or greater than 500 CLKU/mg are considered acceptable and test samples with equal to or greater than 1000 CLKU/mg are considered acceptable. Formulated samples with an uncorrected mortality of greater than 80% at 8% concentration are considered acceptable. Samples with mortality below the established rates are considered inadequate and should be removed from further downstream processing.

TABLE 8

Comparison of efficacy between DiPel ® and CB4-WDGF-1 toward Cabbage Looper Mortality

| Set A | Day 4 LC50 | Day 4 CLKU | Uncorrected Mortality @ 2% | Uncorrected Mortality @ 8% |
|---|---|---|---|---|
| CB4-WDGF-1 | 1.96 | 19831 | 63.16 | 100 |
| Standard | 3.62 | 10759 | 23.53 | 91.18 |
| DiPel ® | 05 | N/A | N/A | N/A |

Example 5: Water Dispersible Granules Using *Pseudomonas fluorescens*

Preparation of *Pseudomonas fluorescens* DM8 WDGF-1 product (hereinafter referred to as "DM8 WDGF-1"): A) Fermentation solids of *Pseudomonas fluorescens* are mixed according to the following compositions to form an uniform solution; B) A is sprayed onto a carrier to form water dispersible granules by using a fluid bed.

TABLE 9

Composition of DM8 WDGF-1.

| # | Final Dried Contents: Active Whole Cell Broth | Carrier Verge N-100 | Stabilizer Nlok | Dispersant PVP | Filler Maltodextrin | Binder XG | Anti-microbial PS | Dissolution 1-Best 5-Worst |
|---|---|---|---|---|---|---|---|---|
| 1 | 32.7% | 51.8% | 14% | 1.5% | 0% | 0% | 0% | 1 |
| 2 | 26.7% | 62% | 0% | 0.1% | 11.4% | 02% | 0% | 2 |

TABLE 9-continued

Composition of DM8 WDGF-1.

| # | Final Dried Contents Active Whole Cell Broth | Carrier Verge N-100 | Stabilizer Nlok | Dispersant PVP | Filler Maltodextrin | Binder XG | Anti-microbial PS | Dissolution 1-Best 5-Worst |
|---|---|---|---|---|---|---|---|---|
| 3 | 28% | 56% | 14% | 1.4% | 0% | 0% | 0% | 3 |
| 4 | 18.6% | 69.5% | 0% | 0.9% | 0% | 0% | 0.2% | 4 |

Note:
Verge N-1000 is a brand of clay absorbent; Whole cell broth is a source of active ingredient; Nlok is a brand of modified starch; PVP is Polyvinylpyrrolidone; XG is Xanthan Gum; PS is Potassium Sorbate.

Figure 18:
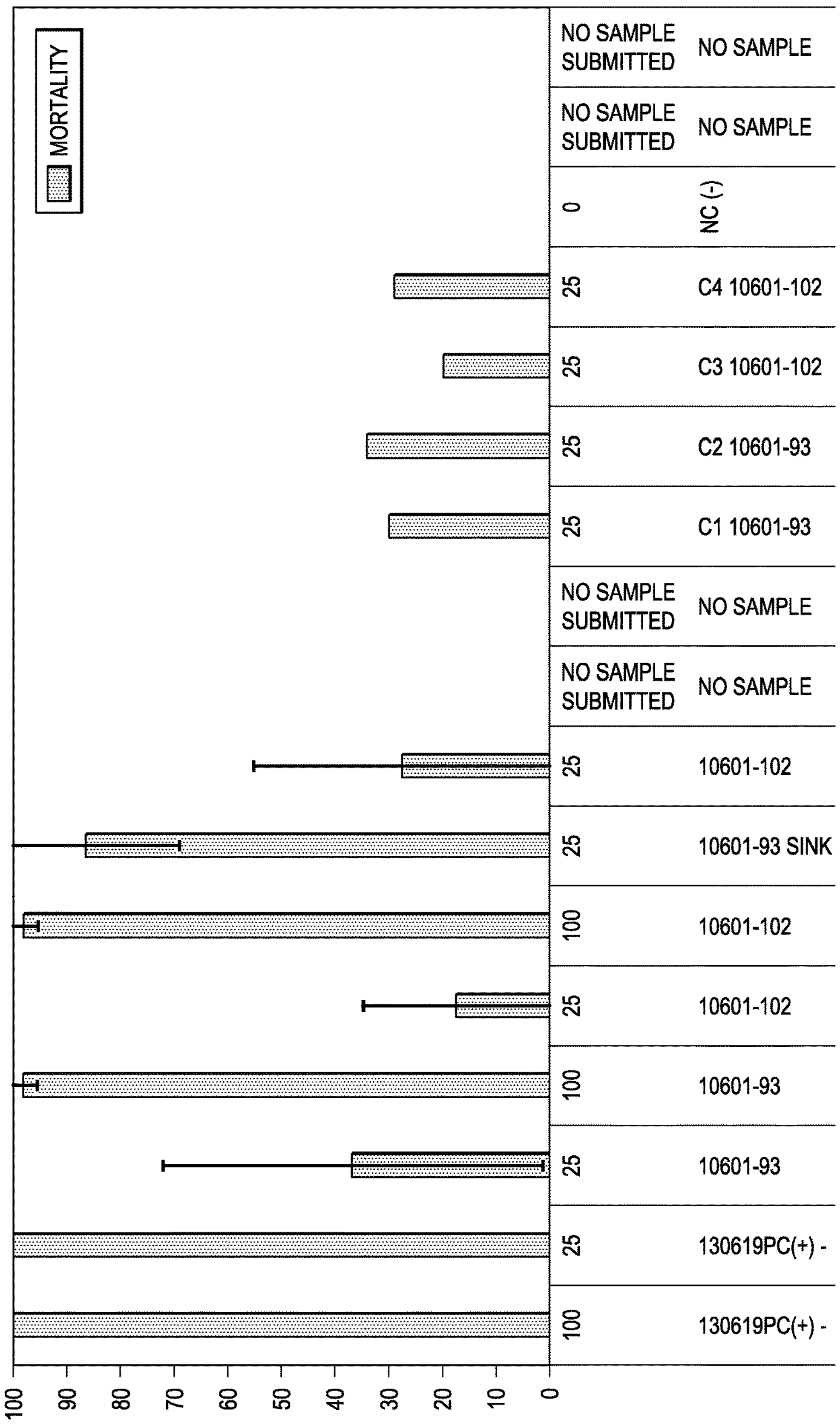
FIG. 18. Efficacy of WDGF using *Pseudomonas fluorescens.*

Mussel bioassay: Add 10 mL of fresh aerated hard water to a clean vial and gently place 10 undamaged mussels into each vial. Pipette appropriate sample volume to achieve the desired concentration into the corresponding vial. Place vials inside a dark cabinet and let the mussels sit undisturbed for 24 hours. Count and record the number of dead mussels in each vial. Pour out half of the water in each vial and rinse mussels with approximately 20 mL of hard water. Continue this each day for up to 15 days. Results are depicted in FIG. 18.

Dispersible Granules (DF)

These are the formulations that use carriers (e.g. kaolin, cellulose, light calcium, white carbon black, silica soil algae) to absorb or stick the active ingredients resulting in dispersible granules for turf application.

Example 6: Dispersible Granules Using *Chromobacterium subtsugae*

Preparation of *Chromobacterium subtsugae* strain PRAA4-1 DGF-1 product (hereinafter referred to as "CB4-DGF-1"): A) Fermentation solids of *Chromobacterium subtsugae* strain PRAA4-1 are mixed according to the following compositions; B) A is sprayed onto a carrier to form dispersible granules by using a fluid bed.

TABLE 10

Composition of CB4 DGF-1 prototype.

| # | Final Dried Contents Active Whole Cell Broth | Carrier D3560 | Dispersant B3A | Dispersant PVP |
|---|---|---|---|---|
| 1 | 27% | 64.3% | 5.8% | 2.9% |

Note:
Whole cell broth is a source of the active ingredient; D3560 is dolomitic limestone; B3A is sodium lignin sulfonate; PVP is Polyvinylpyrrolidine.

Figure 19:
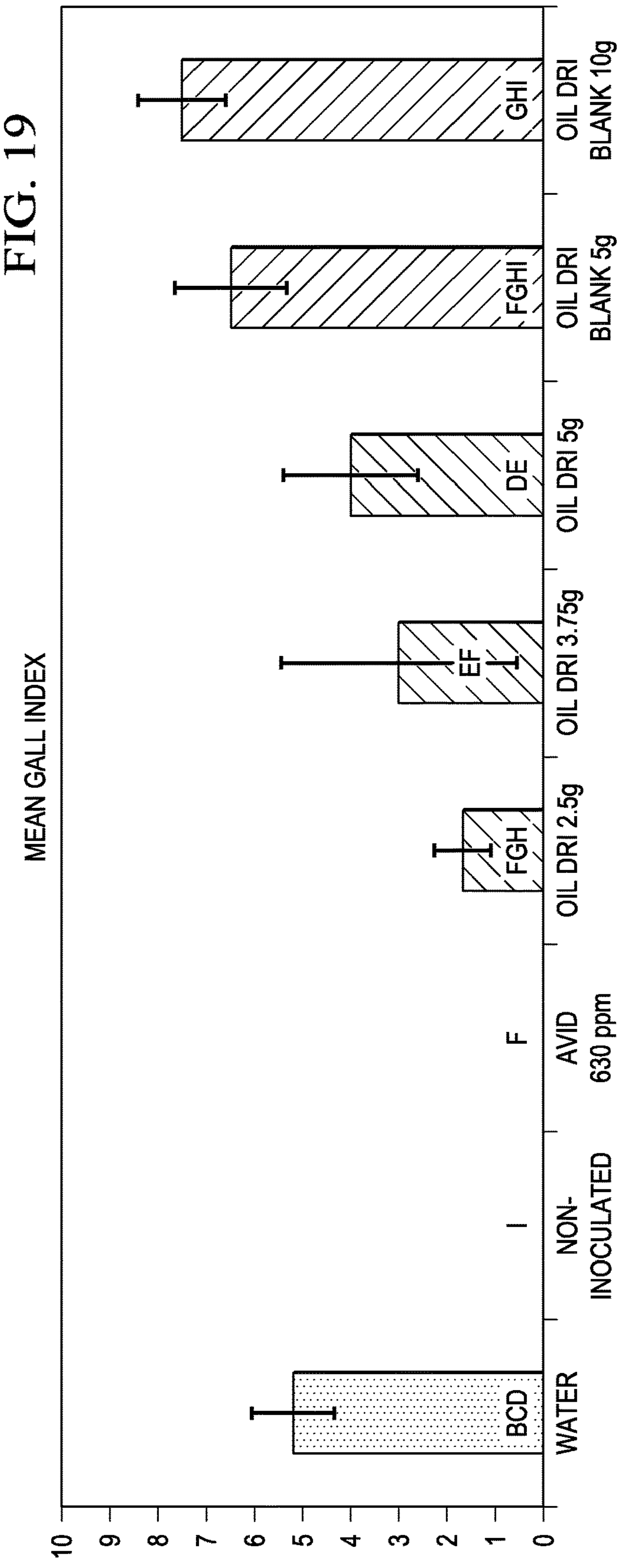
FIG. 19. Efficacy of DG using *Chromobacterium subtsugae.*

Greenhouse cone test: Pick uniform plants for 5 replicates in one treatment group. Drench the cones with 5 mL of each sample based on the treatment list twice to avoid overflowing. Dig 3 holes of ¾ inch depth with a 1 mL pipette tip around each root ¼ inches away from the stem. Change the pipette for digging holes between treatments. Hand water whenever necessary to avoid nematode wash off. Record the data after incubation for 3-4 weeks depending on the temperature of the greenhouse. Results are depicted in FIG. 19.

Evaluation of Physical properties of *Chromobacterium subtsugae* strain PRAA4-1 DGF-1: Dispersion and stability of CB4-DGF-1 was evaluated at 10-fold dilution with tap water (note: 10-fold dilution is recommended application rate). The outer coating completely dissociates in under 2 minutes with negligible amounts of insoluble precipitate. The storage test at 4° C. and 54° C. for 2 weeks showed no physical changes. CB4-DG-1 product was easily spread for turf application.

Cabbage Looper bioassay: The cabbage looper larvae were first instar old when treated. DiPel® from Valent at 100-fold dilution was used as a positive control. Treatments were prepared by applying 100 μL of the solution into a well with one late first instar cabbage looper larvae. Treatments were incubated at 26° C. and LC50 and CLKU (Cabbage Looper Killing Units) were determined 4 days after treatment. The potency of the candidate is determined by comparing LC50s from the candidate and standard using the following equation: Potency (CLKU/mg)=LC50 Standard*potency of standard (CLKU/mg)/LC50 candidate. The potency of standard is 11,000 CLKU/mg. Unformulated broths with equal or greater than 500 CLKU/mg are considered acceptable and test samples with equal or greater than 1000 CLKU/mg are considered acceptable. Formulated samples with an uncorrected mortality of greater than 80% at 8% concentration are considered acceptable. Samples with mortality below the established rates are considered inadequate and should be removed from further downstream processing.

TABLE 11

Comparison of efficacy between DiPel ® and CB4-DGF-1 toward Cabbage Looper Mortality

| Set A | Day 4 LC50 | Day 4 CLKU | Uncorrected Mortality @ 2% | Uncorrected Mortality @ 8% |
|---|---|---|---|---|
| CB4 DGF-1 | 2.59 | 15036 | 250 | 92.50 |
| STD 130927B11 | 3.55 | N/A | 12.50 | 86.84 |
| DiPel ® | 08 | N/A | N/A | N/A |

Example 7: Dispersible Granule Using *Burkholderia rinojensis*

Preparation of *Burkholderia rinojensis* BM3 DGF-1 product (hereinafter referred to as "BM3 DGF-1"): A) Fermentation solids of *Burkholderia rinojensis* are mixed according to the following compositions; B) A is sprayed onto a carrier to form dispersible granules by using a fluid bed.

TABLE 12

| Composition of BM3 DGF-1. | | |
|---|---|---|
| | Final Dried Contents | |
| # | Active Whole Cell Broth | Carrier Verge S-100 |
| 1 | 6.83% | 93.17% |

Note:
Whole cell broth is a source of the active ingredient; Verge S-100 is a brand of clay absorbent.

Figure 20:
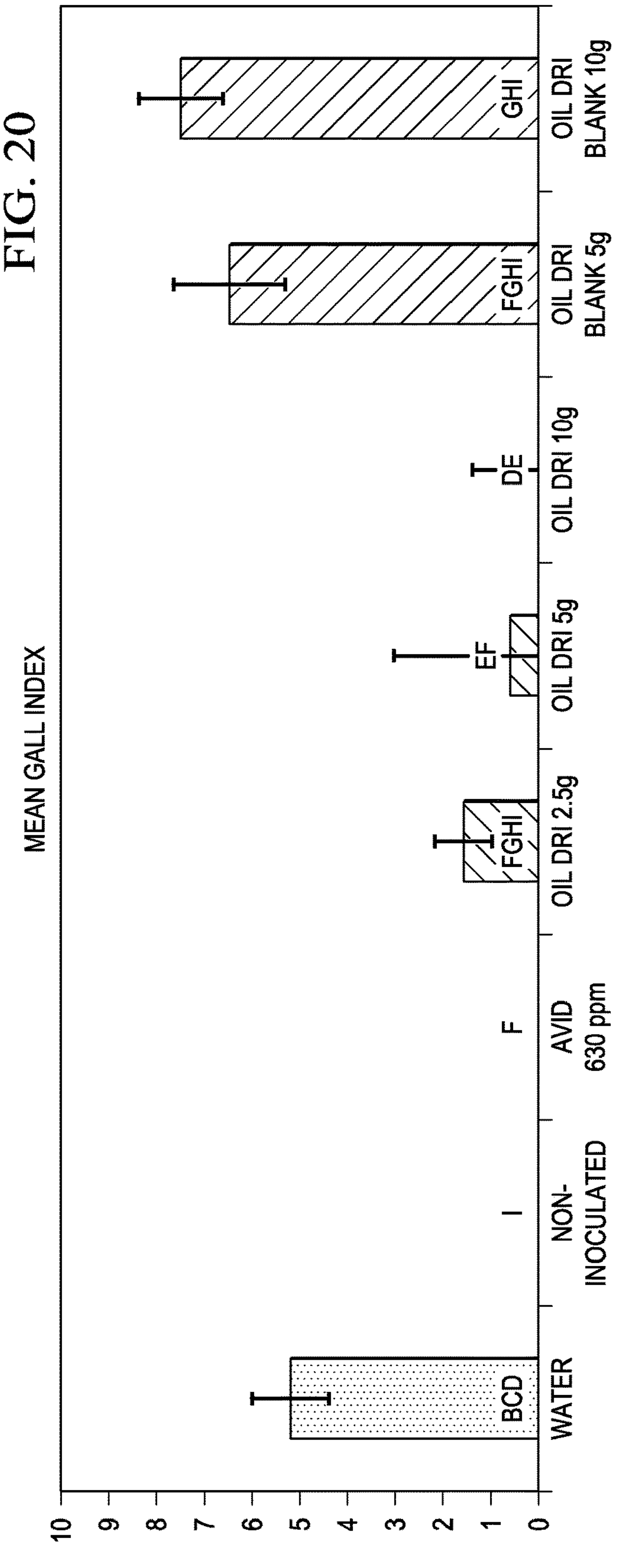
FIG. 20. DG using *Burkholderia rinojensis* displays good efficacy.

Greenhouse cone test: Pick uniform plants for 5 replicates in one treatment group. Drench the cones with 5 mL of each sample based on the treatment list twice to avoid overflowing. Dig 3 holes in ¾ inch depth with a 1 mL pipette tip around each root ¼ inches away from the stem. Change the pipette for digging holes between treatments. Hand water whenever necessary to avoid nematode wash off. Record the data after incubation for 3-4 weeks depending on the temperature of the greenhouse. Results are depicted in FIG. 20.

Evaluation of Physical properties of *Burkholderia rinojensis* strain PRAA4-1 DGF-1: The dispersion and stability of BM3-DGF-1 was evaluated at 10-fold dilution with tap water (note: 10-fold dilution is recommended application rate). The outer coating completely dissociates in under 2 minutes with a negligible amount of insoluble precipitate. Storage tests at 4° C. and 54° C. for 2 weeks showed no physical changes. BM3-DGF-1 product was easily spread for turf application.

Beet Armyworm bioassay: The Beet Armyworm larvae were first instar old when treated. Xentari from Valent at 053 g/10 mL dH2O was used as a positive control. Treatments were prepared by applying 100 μL of the solution into a well with one late first instar beet armyworm larvae. Treatments were incubated at 26° C. and LC50 and BAWKU (Beet Armyworm Killing Units) were determined 4 days after treatment. The potency of the candidate is determined by comparing LC50's from the candidate and standard using the following equation: Potency (BAWKU/mg)=LC50 Standard*potency of standard (BAWKU/mg)/LC50 candidate. The potency of standard is 10,000 BAWKU/mg. Unformulated broths with equal or greater than 500 BAWKU/mg are considered acceptable and test samples with equal or greater than 1500 BAWKU/mg are considered acceptable. Formulated samples with an uncorrected mortality of greater than 80% at 8% concentration are considered acceptable. Samples with mortality below the established rates are considered inadequate and should be removed from further downstream processing.

TABLE 13

Comparison of efficacy between Xentari and BM3 DGF-1 toward Beetarmy Rootwoorm Mortality

| | Day 4 | | Uncorrected Mortality @ | Uncorrected Mortality @ |
|---|---|---|---|---|
| Set A | LC50 | BAWKUKU | 2% | 8% |
| BM3 DGF-1 (1X) | 0.18 | 7970 | 34.21 | 100 |
| BM3 DGF-1 (0.5X) | 0.42 | 3331 | 00 | 92.50 |
| HK STD 130820B | 0.14 | N/A | 41.67 | 100 |
| Xentari | 4.95 | N/A | N/A | N/A |

Example 8: Comparison of Different Formulations of *Chromobacterium subtsugae*

Different formulations of *Chromobacterium subtsugae* were selected for additional field efficacy test. More specifically, the formulations with the better dissolution factors (e.g., <2) were chosen for comparative field trial analysis. Table 14 below shows their composition.

TABLE 14

Compositions of Different formulations of *Chromobacterium subtsugae*

| Compositions | Grandevo | DF7 | DF8 | DF12 | WDGE 1 |
|---|---|---|---|---|---|
| TGAI (Dry weight) | 30% | 30% | 30% | 30% | 30% |
| Clay (Kamin 80B) | 28.25% | 29% | 29% | 34% | 15% |
| Lignin sulphonate (Borresperse 3A) | 40% | 10% | 10% | 15% | 5% |
| Sodium Lauryl Sulfate | 0 | 2% | 10% | 0 | 5% |
| Morwet | 0 | 8% | 0 | 0 | 0 |
| Ammonium sulfate | 0 | 20% | 20% | 20% | 20% |
| Lecithin | 0.75% | 0% | 0% | 0% | 0% |
| Antifoam | 0 | 0% | 0% | 0% | 0% |
| Cabosil | 1% | 1% | 1% | 1% | 0% |
| Microcrystalline Cellulose | 0 | 0% | 0% | 0% | 15% |
| Croscarmellose Sodium | 0% | 0% | 0% | 0% | 10% |

Figure 21:
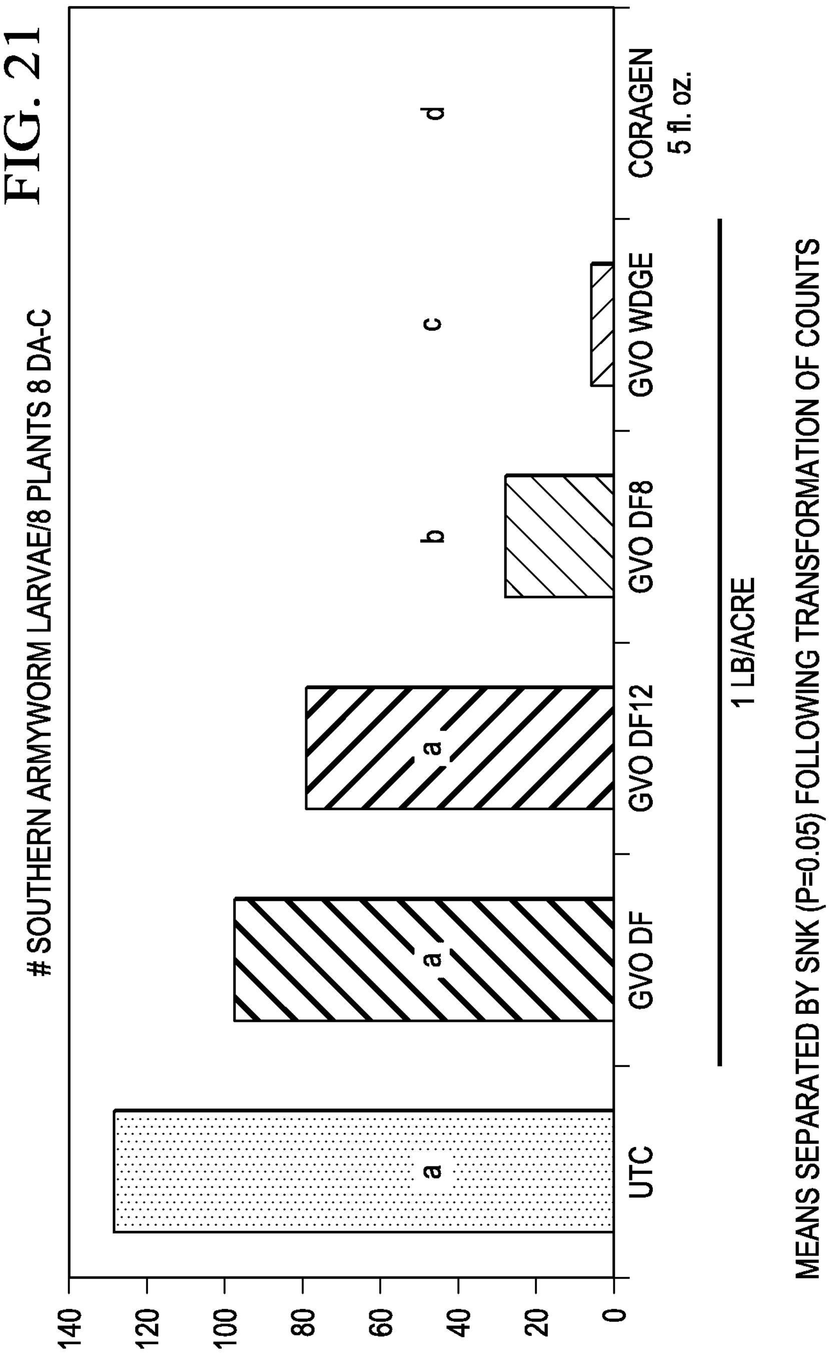
FIG. 21. Control of Southern armyworm on Tomatoes with Various Formulations of *Chromobacterium subtsugae.*
Figure 22:
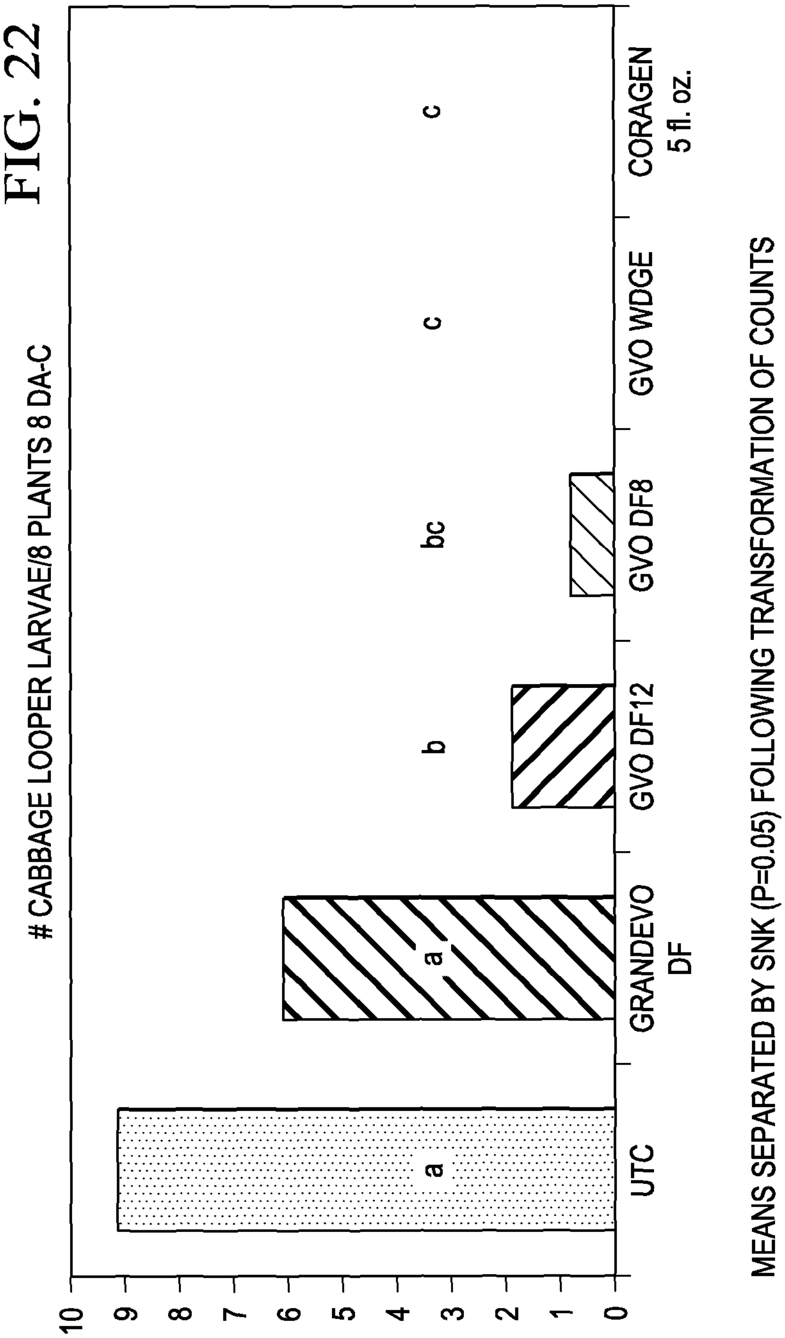
FIG. 22. Control of Cabbage looper larvae on Tomatoes with Various Formulations of *Chromobacterium subtsugae.*

DF3: Commerical Grandevo instantized with lecithin
DF7: Contains Sodium Alklynaphthalenesulfonate formaldehyde condensate (Trade name: Morwet or Armak)
DF8: SLS formulation without lecithin and antifoam
DF12: Dry mi0ing of lignin sulfonate and ammonium sulfate with TGAI and clay
WDGE-1: Water dispersible granule A study was conducted to determine the efficacy of different formulations of bioinsecticides based on *Chromobacterium subtsugae* on controlling southern armyworm (*Spodoptera eridania*) and cabbage looper (*Trichoplusia ni*) in tomato fields (*Solanum lycopersicum*) (FIGS. 21 and 22). The study consisted of six treatments: four formulations of *C. subtsugae* (DF3 (Grandevo®), DF8, DF12, and WDGE-1 at a rate of 1 lb/acre), as well as a non-treated control and the commercial-standard Coragen (rynaxypyr at 5 fl oz/acre of commercial product). Each formulation was applied three times individually (applications A, B and C) on a weekly interval starting on week 6 after transplanting. A tractor-mounted sprayer delivering a water volume of 100 gal/acre was utilized to apply the insecticides. The study was conducted in a randomized complete block design with six replications, with sampling units of eight plants per plot. Populations of southern armyworm and cabbage looper were counted in each experimental unit to assess damage and it occurred 8 days after application C. Data indicated that there were significant differences ($P<0.05$) in the larva populations of both species. For southern armyworm, there were no significant population differences among the non-treated control, and the DF3 and DF12 formulations with population counts ranging between 78 and 129 larvae/8 plants. In contrast, commercially-acceptable control of southern armyworm (below 10 larvae/8 plants) occurred in plots treated either with Coragen (0 larvae/8 plants=100% control) and the WDGE-1 formulation of the bioinsecticide (7 larvae/8 plants=95% control). With regards to cabbage looper control, there were no differences among the DF8 and WDGE formulations of *C. subtsugae* and the commercial standard, all of which had less than 1 larvae/8 plants, with the WDGE formulation and Coragen providing 100% control of this pest.

Initially, it is expected that the field efficacy would be statically similar due to their similar (e.g., fast) dissolution properties. However, this is not the case. FIGS. 21-22 show that WDGE-1 of *Chromobacterium subtsugae* has a surprising high field efficacy in the comparative test.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A water dispersible granule comprising
about 30 weight percent of fermentation solids from *Chromobacterium subtsugae,*
about 15 weight percent clay,
about 5 weight percent lignin sulfonate,
about 5 weight percent Sodium Lauryl Sulfate,
about 20 weight percent Ammonium Sulfate,
about 15 weight percent Microcrystalline Cellulose, and
about 10 weight percent of Croscarmellose Sodium.

2. A method of treating plants comprising the steps of:
obtaining the composition from claim 1;
mixing the composition with water; and
spraying said composition to one or more plants or substrates.

3. The method of claim 2, wherein said plant comprise sugar beet.

4. The method of claim 2, wherein said plant is a grain crop.

5. The method of claim 4, wherein said grain crop comprises soy, wheat, rice, or corn.

6. A method of making an extrusion granule comprising the steps of
providing the water dispersible granule of claim 1; and
extruding the water dispersible granule through an extruder.

7. The method of claim 6, further comprising drying the water dispersible granule before extruding the water dispersible granule through an extruder.

* * * * *